United States Patent [19]

Cyrus et al.

[11] 4,079,137
[45] Mar. 14, 1978

[54] N-BENZHYDRYL-3-METHYL-3-(DIALKOXY)BENZYL-PIPERAZINES

[75] Inventors: Richard Cyrus, Ludwigshafen; Manfred Raschack, Weisenheim am Sand, both of Germany

[73] Assignee: Knoll A.G. Chemische Fabriken, Ludwigshafen am Rhein, Germany

[21] Appl. No.: 760,722

[22] Filed: Jan. 19, 1977

[30] Foreign Application Priority Data

Feb. 7, 1976 Germany .............................. 2604845

[51] Int. Cl.² ................... A61K 31/495; C07D 241/04
[52] U.S. Cl. .............................. 424/250; 260/268 BZ; 260/268 MK
[58] Field of Search ................... 260/268 BZ; 424/250

[56] References Cited

U.S. PATENT DOCUMENTS 3,472,856  10/1969  Archer .......................... 260/268 BZ
3,996,360  12/1976  Cyrus et al. ................... 260/268 BZ
4,031,216  6/1977  Cyrus et al. ...................... 260/268 R

*Primary Examiner*—Richard J. Gallagher
*Assistant Examiner*—Jose Tovar
*Attorney, Agent, or Firm*—Curtis, Morris & Safford

[57] ABSTRACT

Piperazine compounds of the formula

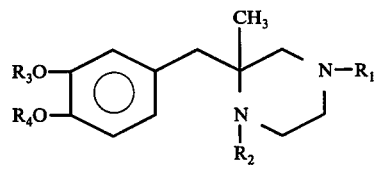

and salts thereof with physiologically tolerable acids useful for the treatment of vascular and cardiac diseases, are disclosed, as are methods for making the compounds and pharmaceutical compositions containing the compounds.

37 Claims, No Drawings

N-BENZHYDRYL-3-METHYL-3-(DIALKOXY)BENZYL-PIPERAZINES

The present invention relates to piperazine derivatives, to methods for their preparation, and to pharmaceutical compositions containing these compounds.

It is known that life-threatening ventricular disturbances of the cardiac rhythm and coronary heart diseases often occur within a narrow time span or are linked by a common cause [cf. F. Nager, et al., Schweiz. med. Wschr. 102, 1836–1851 (1972)]. The medicaments which are available for treatment of symptoms of this sort either are effective against only cardiac arrhythmia (e.g. Lidocain) or only against coronary pain (e.g. nitroglycerin).

The present invention relates to piperazine derivatives of the formula

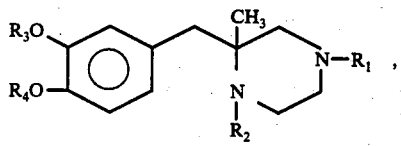

wherein $R_1$ is diphenylmethyl or diphenylmethyl in the phenyl groups of which a hydrogen atom may be replaced by fluorine, $R_2$ is hydrogen or hydrocarbon having 1–5 carbon atoms, which hydrocarbon may be substituted by amino or hydroxy, and $R_3$ and $R_4$ are hydrogen or alkyl having 1–4 carbon atoms, but wherein, however, one of $R_3$ and $R_4$ must be hydrogen, if $R_1$ is diphenylmethyl, as well as salts of these compounds with physiologically tolerable acids.

A further object of the invention is a method of preparing the above-identified compounds, which method comprises reducing a compound of the formula

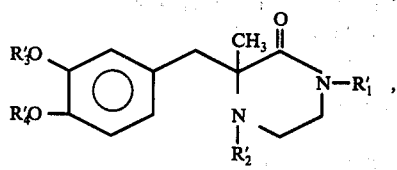

wherein $R'_1$ has the same meaning as above or is hydrogen, $R'_2$ is the same as $R_2$ or may also be benzyl or an acyl group, and $R'_3$ and $R'_4$ are the same as $R_3$ and $R_4$ or may also be acyl, with a metallo-organic compound. In case $R'_2$ is benzyl, the latter is removed by hydrogenation. In case $R'_1$, $R'_2$, $R'_3$ or $R'_4$ in the compounds so obtained are hydrogen, substituents may be introduced onto nitrogen or oxygen. The substances so obtained are, if desired, converted into their salts with physiologically tolerable acids.

Finally, the present invention relates to pharmaceutical compositions which contain compounds of the aforementioned formula or their salts with physiologically tolerable acids.

As physiologically tolerable acids, hydrochloric acid, sulfuric acid, phosphoric acid, acetic acid, malonic acid, succinic acid, citric acid, tartaric acid, lactic acid, and diamidosulfonic acid, among others, can be used.

The reduction of the piperazinone derivatives to the corresponding piperazines can be carried out with, for example, lithium aluminum hydride or dibutyl aluminum hydride in ethers, preferably diethyl- or di-isopropyl ether, or in a cyclic ether such as tetrahydrofuran or dioxane. It is recommended to work at higher temperatures, preferably at the boiling temperatures of the solvents employed.

The alkylation of the piperazine ring system with substituted or unsubstituted diphenylmethyl halides takes place specifically at the nitrogen atom in the 1-position. As halides, the bromides and chlorides preferably are employed. As solvents, aromatic hydrocarbons such as benzene, toluene, and xylene, or low-boiling ketones such as acetone, methyl-ethyl ketone, and di-isobutyl ketone are used. Also suitable are, for example, dimethylformamide and hexamethylphosphoric acid triamide. The temperatures are preferably between 25° C. and 130° C. It is recommended to add basic condensation agents, such as tertiary organic bases or alkali carbonates, for example potassium carbonate or sodium carbonate.

An alkylation at the nitrogen atom in the 4-position can take place in an analogous fashion. When alkyl chlorides or alkyl bromides are used, the addition of sodium iodide or potassium iodide and the use of a small excess pressure of about 1.5–10 atmospheres gauge are recommended.

The further possibility exists of acylating the piperazine ring system with acyl halides, anhydrides, or esters at the nitrogen atom in the 4-position and reducing the acylation products in aliphatic or cyclic ethers — such as diethyl ether, dioxane, or tetrahydrofuran — by means of complex hydrides to form the corresponding alkyl derivatives.

A methyl group can also be introduced onto the nitrogen atom in the 4-position by reacting the piperazine in suitable solvents, such as aromatic hydrocarbons or halohydrocarbons, in the presence of a base, preferably triethylamine, with a haloformic acid ester at low temperatures. The acylation products so obtained can be reduced very readily in a known fashion with complex hydrides.

The reaction with acylating agents can also be carried out already with the piperazinones. During the reduction of the CO-group in the 2-position, an acyl group in the 4-position is reduced at the same time and converted into an alkyl group.

The piperazine derivatives can further be hydroxyalkylated with alkylene oxides at the nitrogen atom in the 4-position. Mixtures of low-boiling alcohols and aromatic hydrocarbons, preferably methanol and benzene in a ratio of 2:1, serves as the solvent. The reaction is suitably carried out at 25° C. - 80° C. and at a pressure of 3–5 atmospheres.

In these reactions at the 4-nitrogen atom, the nitrogen atom in the 1-position must either already be substituted by group $R_1$ or by a protective group which later is cleaved, since otherwise the same reaction would occur at the 1-nitrogen atom as occurs at the 4-nitrogen atom.

The preparation of piperazine derivatives with free hydroxy groups on the benzene ring is particularly successful if one proceeds from piperazinones having protected hydroxy groups. Those groups which can be readily cleaved under reductive conditions and can be removed upon reduction of the keto group, such as, for instances, acetyl groups, are particularly suitable as protective groups.

As is shown in following Table 1 the new compounds inhibit the vasoconstricting effects of numerous biogenic amines and other vasoconstrictors.

TABLE 1

| Substance | Dose (M) | A Histamine | A Adrenalin | B Calcium | C Serotonin |
|---|---|---|---|---|---|
| I | $10^{-7}$ | − 29% | − 59% | − 16% | − 32% |
| II | $10^{-7}$ | − 23% | − 36% | − 24% | − 12% |
| III | $10^{-7}$ | − 23% | − 38% | − 7% | − 32% |
| Vincamine | $10^{-6}$ | − 5% | + 6% | + 3% | 0% |
| Piribedil | $10^{-6}$ | − 4% | + 9% | − 2% | + 4% |
| Pentoxyfyllin | $10^{-6}$ | + 1% | − 5% | − 2% | + 3% |

I = (L)-1-(p-fluorophenyl-phenylmethyl)-3-methyl-3-(3,4-dimethoxybenzyl)-4-methylpiperazine.
II = (L)-1-(p,p'-difluorodiphenylmethyl)-3-methyl-3-(3,4-dimethoxybenzyl)-4-methylpiperazine.
III = (L)-1-(p-fluorophenyl-phenylmethyl)-3-methyl-3-(3,4-dimethoxybenzyl)-piperazine.

In Table 1, under A, is reported how strongly the test substance, in the dose indicated, inhibits the reduction in circulation in a perfused rabbit ear induced by histamine (1.5 × $10^{-6}$ M) or adrenalin (3 × $10^{-8}$ M) [method modified after: Aust. J. exp. Biol. med. Sci. 46, 739 (1968)]. Column B shows to what degree the contraction induced by a 5 × $10^{-4}$ M calcium chloride solution in calcium-deprived and potassium-depolarized strips of blood vessel (rat aorata) is inhibited [method in imitation of: Brit. J. Pharmac. 36, 549 (1969)]. Under C, the corresponding values for serotonin-antagonism are given, as measured in Krebs-Henseleit solution on strips of blood vessel. The values indicate how strongly the contraction brought about by $10^{-6}$ M serotonin is inhibited by the test substance.

The new compounds further possess a good antiarryhthmic efficacy, as can be demonstrated by determination of the functional refractory time in the isolated left guinea-pig auricle using the method of Govier [cf. J. Pharm. Exp. Ther. 148, 100 (1965)].

Table 2 shows the data so obtained. RP signifies the increase in the refractory time in percent.

TABLE 2

| Substance | Dose (M) | RP |
|---|---|---|
| I | $10^{-5}$ | 34 |
| II | $10^{-5}$ | 36 |
| III | $10^{-5}$ | 29 |
| IV | $10^{-5}$ | 69 |
| V | $10^{-5}$ | 73 |
| Vincamine | $10^{-5}$ | 21 |
| Piribedil | $10^{-5}$ | 4 |
| Pentoxyfyllin | $10^{-5}$ | 0 |

I, II, III - See Table 1.
IV = (D)-1-diphenylmethyl-3-methyl-3-(3-hydroxy-4-methoxybenzyl)-4-methylpiperazine.
V = (D)-1-diphenylmethyl-3-methyl-3-(3-methoxy-4-hydroxybenzyl)-4-methylpiperazine.

The new compounds thus are well adaptable to the treatment of vascular diseases such as peripheral and cerebral circulatory disturbances. Further, because of their calcium-antagonistic properties and their refractory time-lengthening properties, they can be used for the treatment of coronary cardiac diseases and the disturbances of the cardiac rhythm which are associated therewith.

The new compounds and their salts are to be administered orally and parenterally. The daily dose is between about 0.1-3.0 mg/kg for intravenous or intramuscular administration and between about 0.5-10 mg/kg for oral administration. For administration, the known galenic dosage unit forms such as tablets, dragées, capsules, and solutions are suitable.

A better understanding of the present invention and of its many advantages will be had by referring to the following specific examples, given by way of illustration. Introductory Examples A-L pertain to the preparation of starting materials.

EXAMPLE A

By the reaction of 3,4-dihydroxyphenyl-α-alanine methyl ester with benzyl bromide in methyl-ethyl ketone under reflux, N-benzyl-3,4-dibenzyloxyphenyl-α-alanine methyl ester is obtained (m.p.$_{HCl}$ = 170° C.), which forms N-benzyl-N-cyanomethyl-3,4-dibenzyloxyphenyl-α-alanine methyl ester (m.p. = 107° C.) in the cold with aqueous formaldehyde solution and potassium cyanide. From this, 3-methyl-3-(3,4-dibenzyloxyphenyl)-4-benzyl-piperazinone-(2), (m.p. = 155° C.), is obtained by hydrogenation with H$_2$/Raney-cobalt under pressure, from which, using concentrated hydrobromic acid at room temperature, is obtained 3-methyl-3-(3,4-dihydroxybenzyl)-4-benzylpiperazinone-(2)-hydrobromide (Aa) (m.p. = 161° - 163° C.).

In an analogous fashion are obtained:
AaD)
   (D)-3-methyl-3-(3,4-dihydroxybenzyl)-4-benzyl-piperazinone-(2)-hydrobromide
   m.p. = 155° - 157° C. (isopropanol)
   $[\alpha]_D^{20}$ = + 14.2° (c = 1, methanol)
AaL)
   (L)-3-methyl-3-(3,4-dihydroxybenzyl)-4-benzyl-piperazinone-(2)-hydrobromide
   m.p. = 156° - 158° C. (isopropanol)
   $[\alpha]_D^{20}$ = − 14.3° (c = 1, methanol)

EXAMPLE B

The compounds obtained according to A can be converted to the corresponding 3,4-dialkoxybenzyl compounds with alkyl iodides in acetone and in the presence of potassium carbonate. In this fashion are obtained:
Ba)
   3-methyl-3-(3,4-dimethoxybenzyl)-4-benzylpiperazinone-(2)
   m.p. = 149° C. (methanol)
BaD)
   (D)-3-methyl-3-(3,4-dimethoxybenzyl)-4-benzyl-piperazinone-(2)
   m.p. = 183° C. (methanol)
   $[\alpha]_D^{20}$ = − 24.1° (c = 1, methanol)
BaL)
   (L)-3-methyl-3-(3,4-dimethoxybenzyl)-4-benzyl-piperazinone-(2)
   m.p. = 183° C. (methanol)
   $[\alpha]_D^{20}$ = + 24.1° (c = 1, methanol)
Bb)
   3-methyl-3-(3,4-diethoxybenzyl)-4-benzylpiperazinone-(2)
   m.p. = 134° - 135° C. (isopropanol)
BbD)
   (D)-3-methyl-3-(3,4-diethoxybenzyl)-4-benzyl-piperazinone-(2)
   m.p. = 93° C. (diisopropylether)
   $[\alpha]_D^{20}$ = − 31.1° (c = 1, methanol)
BbL)
   (L)-3-methyl-3-(3,4-diethoxybenzyl)-4-benzyl-piperazinone-(2)
   m.p. = 93° C. (diiopropylether)
   $[\alpha]_D^{20}$ = + 31° (c = 1, methanol)

EXAMPLE C

By catalytic hydrogenation with palladium as the catalyst, the following compounds are obtained from those mentioned above in B:

Ca)
  3-methyl-3-(3,4-dimethoxybenzyl)-piperazinone-(2)
  m.p. = 147° - 148° C. (isopropanol)

CaD)
  (D)-3-methyl-3-(3,4-dimethoxybenzyl)-piperazinone-(2)
  m.p. = 68° - 70° C. (diethylether)
  $[\alpha]_D^{20} = + 41.9°$ (c = 1, methanol)

CaL)
  (L)-3-methyl-3-(3,4-dimethoxybenzyl)-piperazinone-(2)
  m.p. = 68° - 70° C. (diethylether)
  $[\alpha]_D^{20} = - 41.8°$ (c = 1, methanol)

Cb)
  3-methyl-3-(3,4-diethoxybenzyl)-piperazinone-(2)
  m.p. = 115° - 117° C. (isopropanol)

CbD)
  (D)-3-methyl-3-(3,4-diethoxybenzyl)-piperazinone-(2), as an oil
  $[\alpha]_D^{20} = + 32.6°$ (c = 1, methanol)

CbL)
  (L)-3-methyl-3-(3,4-diethoxybenzyl)-piperazinone-(2), as an oil
  $[\alpha]_D^{20} = - 32.5°$ (c = 1, methanol)

EXAMPLE D

From the compounds named in C, the following are obtained by reaction with methyl iodide in the presence of potassium carbonate and dimethylformamide:

Db)
  3-methyl-3-(3,4-diethoxybenzyl)-4-methylpiperazinone-(2)
  m.p. = 81° - 83° C. (diisopropylether)

DbD)
  (D)-3-methyl-3-(3,4-diethoxybenzyl)-4-methylpiperazinone-(2)
  m.p. = 54° - 56° C. (diisopropylether)
  $[\alpha]_D^{20} = + 40.6°$ (c = 1, methanol)

DbL)
  (L)-3-methyl-3-(3,4-diethoxybenzyl)-4-methylpiperazinone-(2)
  m.p. = 55° - 57° C. (diisopropylether)
  $[\alpha]_D^{20} = - 40.3°$ (c = 1, methanol)

Da)
  3-methyl-3-(3,4-dimethoxybenzyl)-4-methylpiperazinone-(2)
  m.p. = 95° C. (diisopropylether)

DaD)
  (D)-3-methyl-3-(3,4-dimethoxybenzyl)-4-methylpiperazinone-(2)
  m.p. = 124° - 126° C. (isopropanol)
  $[\alpha]_D^{20} = + 49.1°$ (c = 1, methanol)

DaL)
  (L)-3-methyl-3-(3,4-dimethoxybenzyl)-4-methylpiperazinone-(2)
  m.p. = 126° C. (isopropanol)
  $[\alpha]_D^{20} = - 49.3°$ (c = 1, methanol)

EXAMPLE E

By reaction of 3-methyl-3-(3,4-dimethoxybenzyl)-4-methylpiperazinone-(2) (Da) with sodium hydride in dimethylformamide and with the addition of p-fluorophenyl-phenylmethylchloride, 1-(p-fluorophenyl-phenylmethyl)-3-methyl-3-(3,4-dimethoxybenzyl)-4-methylpiperazinone-(2) (Ea) is obtained. m.p. = 129° - 131° C. (diisopropylether).

1-(p-fluorophenyl-phenylmethyl)-3-methyl-3-(3,4-dimethoxybenzyl)-piperazinone-(2) (Eb) is obtained in corresponding fashion. m.p. = 111° - 113° C. (diisopropylether).

EXAMPLE F

By the reaction of (D)-3-methyl-3-(3,4-dihydroxybenzyl)-4-benzylpiperazinone-(2) (cf. A) with benzyl bromide according to B, (D)-3-methyl-3-(3,4-dibenzyloxybenzyl)-4-benzylpiperazinone-(2) is obtained. If this compound is reacted with sodium hydride and subsequently with diphenylmethyl bromide in dimethylformamide, (D)-1-diphenylmethyl-3-methyl-3-(3,4-dibenzyloxybenzyl)-4-benzylpiperazinone-(2) (Fa) is obtained (colorless oil, $[\alpha]_D^{20} = - 34.6°$, c = 1, methanol), from which the benzyl groups can be cleaved by hydrogenation with palladium/hydrogen. From the dihydroxybenzyl compound so-obtained, (D)-1-diphenylmethyl-3-methyl-3-(3,4-diacetoxybenzyl)-piperazinone-(2) (FbD) m.p.$_{HCl}$ = 230° - 232° C., isopropanol, $[\alpha]_D^{20} = + 32.2°$ (c = 1, methanol) is obtained by reaction with acetyl chloride in glacial acetic acid/HCl.

In an analogous fashion is obtained:

FbL)
  (L)-1-diphenylmethyl-3-methyl-3-(3,4-diacetoxybenzyl)-piperazinone-(2)
  m.p.$_{HCl}$ = 231° - 233° C. (isopropanol)
  $[\alpha]_D^{20} = - 32.5°$ (c = 1, methanol)

By reaction with methyl iodide and potassium carbonate in acetone, one obtains from these compounds:

FcD)
  (D)-1-diphenylmethyl-3-methyl-3-(3,4-diacetoxybenzyl)-4-methylpiperazinone-(2)
  m.p. = 117° - 119° C. (isopropanol)
  $[\alpha]_D^{20} = + 14.3°$ (c = 1, methanol)

FcL)
  (L)-1-diphenylmethyl-3-methyl-3-(3,4-diacetoxybenzyl)-4-methylpiperazinone-(2)
  m.p. = 118° - 120° C. (isopropanol)
  $[\alpha]_D^{20} = - 14.5°$ (c = 1, methanol)

EXAMPLE G

By the reaction of 3-methyl-3-(3,4-dimethoxybenzyl)-piperazinone-(2) (Ca) with acyl halides, the corresponding 4-acyl compounds are obtained such as, for example, 3-methyl-3-(3,4-dimethoxybenzyl)-4-carbethoxypiperazinone-(2) (Ga).
  m.p. = 162° - 164° C. (isopropanol).

From this compound, one obtains according to E, 1-(p-fluorophenyl-phenylmethyl)-3-methyl-3-(3,4-dimethoxybenzyl)-4-carbethoxypiperazinone-(2) (Gb).
  m.p. = 135° - 137° C. (isopropanol).

EXAMPLE H

By the reaction of (D)-1-diphenylmethyl-3-methyl-3-(3,4-dibenzyloxybenzyl)-4-benzylpiperazinone-(2) (Fa) with concentrated hydrobromic acid, (D)-1-diphenylmethyl-3-methyl-3-(3,4-dihydroxybenzyl)-4-benzylpiperazinone-(2) (HaD) is obtained.
  m.p. = 225° - 227° C. (isopropanol),
  $[\alpha]_D^{20} = - 78.8°$ (c = 1, methanol)

Analogously, one obtains the corresponding (L)-compound (HaL).
  m.p. = 224° - 226° C. (isopropanol)

$[\alpha]_D^{20} = + 78.4°$ (c = 1, methanol)

EXAMPLE I (L)-1-diphenylmethyl-3-methyl-3-(3,4-dihydroxybenzyl)-4-benzylpiperazinone-(2)-hydrobromide (HaL) is reacted in an acetone with an equimolar amount of methyl iodide in the presence of potassium carbonate. The product so obtained is purified and hydrogenated in the presence of palladium black. The reaction mixture is filtered, concentrated, and taken up in diethyl ether. The solution is made alkaline with ammonium hydroxide solution, extracted with water, and concentrated to dryness. The residue is dissolved in diethyl ether and extracted with diluted sodium hydroxide. The ethereal solution contains (L)-1-diphenylmethyl-3-methyl-3-(3,4-dimethoxybenzyl)-piperazonine-(2), m.p. = 167° C. (isopropanol). The aqueous solution is combined with ammonium chloride and extracted with diethyl ether. The combined extracts contain a mixture of (L)-1-diphenylmethyl-3-methyl-3-(3-hydroxy-4-methoxybenzyl)-piperazinone-(2) (IaL) and (L)-1-diphenylmethyl-3-methyl-3-(3-methoxy-4-hydroxybenzyl)-piperazinone-(2) (IbL), which can be separated by recrystallization from isopropanol.

IaL) (m.p. = 159° - 161° C. $[\alpha]_D^{20} = + 5.4°$) precipitates as crystals, whereas (IbL) remains in the solution and precipitates after concentration in the form of an impure amorphous powder.

In the same manner, the corresponding D-enantiomers are obtained, IaD (m.p. = 158° - 160° C., $[\alpha]_D^{20} = - 5.3°$).

EXAMPLE K 13.1 g of 3-methyl-3-(3,4-diethoxybenzyl)-4-methylpiperazinone-(2) (Da) in 100 ml of tetrahydrofuran is added dropwise over the course of an hour to a suspension of 5 g of lithium aluminum hydride in 300 ml of tetrahydrofuran at the boiling point, with stirring. The suspension is kept at boiling for a further 2 hours with stirring. After the careful addition of water, the mixture is filtered and the filtrate is reduced to dryness in vacuum and distilled.

11.2 g (90%) of 3-methyl-3-(3,4-diethoxybenzyl)-4-methylpiperazine (Ka) are obtained.
b.p. = 160° - 163° C. (0.01 mm Hg)
In the same fashion are obtained:
KaD)
(D)-3-methyl-3-(3,4-diethoxybenzyl)-4-methylpiperazine
b.p. = 160° - 162° C. (0.01 mm Hg)
$[\alpha]_D^{20} = - 20.8°$ (c = 1, methanol)
KaL)
(L)-3-methyl-3-(3,4-diethoxybenzyl)-4-methylpiperazine
b.p. = 160° - 162° C. (0.01 mm Hg)
$[\alpha]_D^{20} = + 21.0°$ (c = 1, methanol)
Kb)
3-methyl-3-(3,4-dimethoxybenzyl)-4-methylpiperazine
b.p. = 162° - 165° C. (0.05 mm Hg)
KbD)
(D)-3-methyl-3-(3,4-dimethoxybenzyl)-4-methylpiperazine
b.p. = 164° - 166° C. (0.7 mm Hg)
$[\alpha]_D^{20} = - 22.9°$ (c = 1, methanol)
KbL)
(L)-3-methyl-3-(3,4-dimethoxybenzyl)-4-methylpiperazine
b.p. = 164° - 166° C. (0.5 mm Hg)
$[\alpha]_D^{20} = + 22.7°$ (c = 1, methanol)
KcD)
(D)-1-diphenylmethyl-3-methyl-3-(3-hydroxy-4-methoxybenzyl)-piperazine
m.p. = 217° - 219° C. (ethanol)
$[\alpha]_D^{20} = + 29.5°$ (c = 1, chloroform)
KcL)
(L)-1-diphenylmethyl-3-methyl-3-(3-hydroxy-4-methoxybenzyl)-piperazine
m.p. = 218° - 220° C. (ethanol)
$[\alpha]_D^{20} = - 29.3°$ (c = 1, chloroform)
KdD)
(D)-1-diphenylmethyl-3-methyl-3-(3-methoxy-4-hydroxybenzyl)-piperazine
m.p. = 185° - 187° C. (isopropanol)
$[\alpha]_D^{20} = + 19.0°$ (c = 1, methanol)
KdL)
(L)-1-diphenylmethyl-3-methyl-3-(3-methoxy-4-hydroxybenzyl)-piperazine
m.p. = 184° - 186° C. (isopropanol)
$[\alpha]_D^{20} = - 19.2°$ (c = 1, methanol)

The compounds Ka - KbL can be prepared in the same manner from the corresponding 4-carbethoxypiperazinone compounds (cf. Ga). However, for this purpose a larger amount of reducing agent is needed.

EXAMPLE L

A solution of 25 g of 3-methyl-3-(3,4-diethoxybenzyl)-4-benzyl-piperazinone-(2) (Bb) in 100 ml of tetrahydrofuran is slowly added dropwise to a suspension of 7.4 g of lithium aluminum hydride in 300 ml of tetrahydrofuran with stirring at the boiling point. The reaction solution is kept at the boiling point, with stirring, for three hours. After careful decomposition with water, insoluble materials are filtered off and the filtrate is evaporated to dryness. 23.6 g (98.1%) of 3-methyl-3-(3,4-diethoxybenzyl)-4-benzyl-piperazine [m.p. = 94° - 96° C. (diisopropylether)] are obtained and are dissolved in 150 ml of glacial acetic acid, combined with 1.5 g of 10% palladium black, and hydrogenated at room temperature. The catalyst is filtered off, the solution is concentrated to dryness, the residue is taken up in 150 ml of chloroform, and made alkaline with ammonium hydroxide solution. The organic phase is extracted four times with 20 ml portions of water, dried over sodium sulfate, and evaporated to dryness. The oily residue is distilled in vacuum. 15.8 g (89%) of 3-methyl-3-(3,4-diethoxybenzyl)-piperazine (La) are obtained.
b.p. = 160° - 163° C. (0.05 mm Hg).
In the same yields, the following compounds are prepared:
LaD)
(D)-3-methyl-3-(3,4-diethoxybenzyl)-piperazine
b.p. = 172° - 175° C. (0.01 mm Hg)
$[\alpha]_D^{20} = + 12.3°$ (c = 1, methanol)
LaL)
(L)-3-methyl-3-(3,4-diethoxybenzyl)-piperazine
b.p. = 172° - 175° C. (0.01 mm Hg)
$[\alpha]_D^{20} = - 12.5°$ (c = 1, methanol)
Lb)
3-methyl-3-(3,4-dimethoxybenzyl)-piperazine
b.p. = 188° - 190° C. (0.05 mm Hg)
LbD)
(D)-3-methyl-3-(3,4-dimethoxybenzyl)-piperazine
b.p. = 178° - 180° C. (0.05 mm Hg)
$[\alpha]_D^{20} = + 15.5°$ (c = 1, methanol)
LbL)

(L)-3-methyl-3-(3,4-dimethoxybenzyl)-piperazine
b.p. = 178° – 181° C. (0.05 mm Hg)
$[\alpha]_D^{20} = -15.6°$ (c = 1, methanol)

EXAMPLE 1

2.5 g of 3-methyl-3-(3,4-dimethoxybenzyl)-piperazine (2b) are dissolved in 60 ml of dry methyl-ethyl ketone, combined with 2.8 g of dry potassium carbonate and 0.8 g of potassium iodide, and heated to boiling with stirring. A solution of 2.25 g of 4-fluorophenyl-phenylmethyl chloride in 10 ml of methyl-ethyl ketone is slowly added thereto dropwise. Thereafter, the mixture is heated at boiling for 24 hours under reflux and with stirring. The mixture is filtered and the filtrate reduced in volume. The residue is taken up in toluene and washed free of halogen with water. The organic phase is evaporated to dryness in vacuum, the oily residue is dissolved in diethyl ether, and hydrogen chloride is introduced into the solution. 4.3 g (85%) of 1-(p-fluorophenyl-phenylmethyl)-3-methyl-3-(3,4-dimethoxybenzyl)-piperazine-dihydrochloride (1a) precipitate. m.p. = 188° – 190° C. (acetone)

In the same yield, the following compounds are obtained in corresponding fashion:

1aD)
(D)-1-(p-fluorophenyl-phenylmethyl)-3-methyl-3-(3,4-dimethoxybenzyl)-piperazine, as a glassy solidified resin
$[\alpha]_D^{20} = + 16.1°$ (c = 1, methanol)

1aL)
(L)-1-(p-fluorophenyl-phenylmethyl)-3-methyl-3-(3,4-dimethoxybenzyl)-piperazine, as a glassy solidified resin
$[\alpha]_D^{20} = - 16.5°$ (c = 1, methanol)

1b)
1-(p,p'-difluorodiphenylmethyl)-3-methyl-3-(3,4-dimethoxyphenyl)-piperazine-dihydrochloride
m.p. = 175° – 178° C. (isopropanol)

1bD)
(D)-1-(p,p'-difluorodiphenylmethyl)-3-methyl-3-(3,4-dimethoxybenzyl)-piperazine, as a glassy solidified resin
$[\alpha]_D^{20} = + 16.0°$ (c = 1, methanol)

1bL)
(L)-1-(p,p'-difluorodiphenylmethyl)-3-methyl-3-(3,4-dimethoxybenzyl)-piperazine, as a glassy solidified resin
$[\alpha]_D^{20} = - 15.5°$ (c = 1, methanol)

1cD)
(D)-1-(p-fluorophenyl-phenylmethyl)-3-methyl-3-(3,4-diethoxybenzyl)-piperazine, as a glassy solidified resin
$[\alpha]_D^{20} = + 16.1°$ (c = 1, methanol)

1cL)
(L)-1-(p-fluorophenyl-phenylmethyl)-3-methyl-3-(3,4-diethoxybenzyl)-piperazine, as a glassy solidified resin
$[\alpha]_D^{20} = - 16.0°$ (c = 1, methanol)

1d)
1-(p,p'-difluorodiphenylmethyl)-3-methyl-3-(3,4-diethoxybenzyl)-piperazine-dihydrochloride
m.p. = 159° – 161° C. (ethanol)

1dD)
(D)-1-(p,p'-difluorodiphenylmethyl)-3-methyl-3-(3,4-diethoxybenzyl)-piperazine, as a glassy solidified resin
$[\alpha]_D^{20} = + 13.1°$ (c = 1, methanol)

1dL)
(L)-1-(p,p'-difluorodiphenylmethyl)-3-methyl-3-(3,4-diethoxybenzyl)-piperazine, as a glassy solidified resin
$[\alpha]_D^{20} = - 13.3°$ (c = 1, methanol)

EXAMPLE 2

13.2 g of 3-methyl-3-(3,4-dimethoxybenzyl)-4-methylpiperazine (Kb) are dissolved in 300 ml of dry methylethyl ketone, combined with 13.8 g of potassium carbonate, 4.1 g of potassium iodide, and 12 g of p,p'-difluorodiphenylmethyl chloride, and heated to boiling with reflux and stirring for 24 hours. The mixture is filtered and the filtrate is reduced. The residue is taken up in diethyl ether, washed free of halogen with water, dried over magnesium sulfate, and filtered. Hydrogen chloride is introduced into the filtrate. Thereby, 25 g (92.5%) of 1-(p,p'-difluorodiphenylmethyl)-3-methyl-3-(3,4-dimethoxybenzyl)-4-methylpiperazine-dihydrochloride (2a) precipitate as the hydrate. m.p. = 173° – 175° C. (isopropanol).

In the same way and in the same yield the following are obtained:

2aD)
(D)-1-(p,p'-difluorodiphenylmethyl)-3-methyl-3-(3,4-dimethoxybenzyl)-4-methylpiperazine, as a glassy solidified resin
$[\alpha]_D^{20} = - 24°$ (c = 1, methanol)

2aL)
(L)-1-(p,p'-difluorodiphenylmethyl)-3-methyl-3-(3,4-dimethoxybenzyl)-4-methylpiperazine, as a glassy solidified resin
$[\alpha]_D^{20} = + 23.5°$ (c = 1, methanol)

2b)
1-(p-fluorophenyl-phenylmethyl)-3-methyl-3-(3,4-dimethoxybenzyl)-4-methylpiperazine-dihydrochloride
m.p. = 195° – 197° C. (ethanol)

2bD)
(D)-1-(p-fluorophenyl-phenylmethyl)-3-methyl-3-(3,4-dimethoxybenzyl)-4-methylpiperazine, as a glassy solidified resin
$[\alpha]_D^{20} = - 22.8°$ (c = 1, methanol)

2bL)
(L)-1-(p-fluorophenyl-phenylmethyl)-3-methyl-3-(3,4-dimethoxybenzyl)-4-methylpiperazine, as a glassy solidified resin
$[\alpha]_D^{20} = + 22.8°$ (c = 1, methanol)

2cD)
(D)-1-(p-fluorophenyl-phenylmethyl)-3-methyl-3-(3,4-diethoxybenzyl)-4-methylpiperazine
m.p. = 111° – 113° C. (ethanol)
$[\alpha]_D^{20} = - 20.2°$ (c = 1, methanol)

2cL)
(L)-1-(p-fluorophenyl-phenylmethyl)-3-methyl-3-(3,4-diethoxybenzyl)-4-methylpiperazine
m.p. = 111° – 113° C. (ethanol)
$[\alpha]_D^{20} = + 20.0°$ (c = 1, methanol)

2d)
1-(p,p'-difluorodiphenylmethyl)-3-methyl-3-(3,4-diethoxybenzyl)-4-methylpiperazine-dihydrochloride
m.p. = 205° – 207° C. (ethanol)

2dD)
(D)-1-(p,p'-difluorodiphenylmethyl)-3-methyl-3-(3,4-diethoxybenzyl)-4-methylpiperazine
m.p. = 125° – 127° C. (methanol)
$[\alpha]_D^{20} = - 22.2°$ (c = 1, methanol)

2dL)

(L)-1-(p,p'-difluorodiphenylmethyl)-3-methyl-3-(3,4-diethoxybenzyl)-4-methylpiperazine
m.p. = 125° – 127° C. (methanol)
$[\alpha]_D^{20} = + 22.1°$ (c = 1, methanol)

EXAMPLE 3

4.3 g of 1-(p-fluorophenyl-phenylmethyl)-3-methyl-3-(3,4-dimethoxybenzyl)-piperazine (1a) are dissolved in 100 ml of acetone and combined with 1.5 g of potassium carbonate. A solution of 1.45 g of methyl iodide in 20 ml of acetone is added dropwise into the suspension with stirring at 25° C. After stirring for 12 hours at 25° C., the mixture is filtered and the filtrate is evaporated to dryness. The residue is taken up in diethyl ether and washed free of halogen with water. After drying over magnesium sulfate and the introduction of hydrogen chloride, 4.2 g (83%) of 1-(p-fluorophenyl-phenylmethyl)-3-methyl-3-(3,4-dimethoxybenzyl)-4-methylpiperazine-dihydrochloride (2b) precipitate. m.p. = 195° – 197° C. (ethanol).

EXAMPLE 4

10 g of 1-(p-fluorophenyl-phenylmethyl)-3-methyl-3-(3,4-dimethoxybenzyl)-piperazine (1a) are dissolved in 100 ml of benzene and 2.2 g of triethylamine. With stirring, at room temperature, 2.1 g of chloroformic acid ethyl ester in 30 ml of benzene are added dropwise. After 12 hours, the solution is washed free of halogen with water and reduced to dryness.

10.9 g (94%) of 1-(p-fluorophenyl-phenylmethyl)-3-methyl-3-(3,4-dimethoxybenzyl)-4-carbethoxypiperazine are obtained as a colorless oil which is dissolved in 100 ml of dry tetrahydrofuran. This solution is added dropwise, with stirring, over the course of one hour, into a boiling suspension of 2.45 g of lithium aluminum hydride in 120 ml of dry tetrahydrofuran and kept at boiling for a further 3 hours. After careful addition of water, the solution is filtered and the filtrate is reduced to dryness. From the residue, after solution in diethyl ether and the introduction of hydrogen chloride, 8.9 g (80%) of 1-(p-fluorophenyl-phenylmethyl)-3-methyl-3-(3,4-dimethoxybenzyl)-4-methylpiperazine-dihydrochloride (2b) are obtained.
m.p. = 195° – 197° C. (ethanol)

In an analogous fashion are obtained:
4aD)
   (D)-1-diphenylmethyl-3-methyl-3-(3-hydroxy-4-methoxybenzyl)-4-methylpiperazine
   m.p. = 122° – 124° C. (diisopropylether)
   $[\alpha]_D^{20} = - 22.3°$ (c = 1, methanol)
4aL)
   (L)-1-diphenylmethyl-3-methyl-3-(3-hydroxy-4-methoxybenzyl)-4-methylpiperazine
   m.p. = 123° – 125° C. (diisopropylether)
   $[\alpha]_D^{20} = + 22.1°$ (c = 1, methanol)
4bD)
   (D)-1-diphenylmethyl-3-methyl-3-(3-methoxy-4-hydroxybenzyl)-4-methylpiperazine
   m.p.$_{HCl}$ = 180° – 181° C. (isopropanol)
   $[\alpha]_D^{20} = + 7.1°$ (c = 1, methanol)
4bL)
   (L)-1-diphenylmethyl-3-methyl-3-(3-methoxy-4-hydroxybenzyl)-4methylpiperazine
   m.p.$_{HCl}$ = 188° – 190° C. (isopropanol)
   $[\alpha]_D^{20} = - 7°$ (c = 1, methanol)

In the preparation of compounds 4a and 4b, a larger amount of chloroformic acid ethyl ester and lithium aluminum hydride must be added because the free hydroxy group on the benzene ring is esterified by the reaction and again set free.

EXAMPLE 5

9 g of the piperazinone derivative (Ea) is dissolved in 100 ml of tetrahydrofuran and added dropwise with stirring to a boiling suspension of 2.2 g of lithium aluminum hydride in 100 ml of tetrahydrofuran over the course of an hour. After three hours, the bath is decomposed with water, insoluble materials are filtered off, and the filtrate is evaporated to dryness. The oily residue is dissolved in 120 ml of diethyl ether. Hydrogen chloride is introduced and the resulting precipitate is filtered off. 8.8 g (87%) of 1-(p-fluorophenylphenylmethyl)-3-methyl-3-(3,4-dimethoxybenzyl)-4-methylpiperazinedihydrochloride (2b) are obtained. m.p. = 195° – 197° C. (ethanol).

In an analogous fashion, the compounds mentioned in Examples 2 and 4 are obtained.

EXAMPLE 6

8.1 g of the piperazinone derivative (Gb) are dissolved in 50 ml of tetrahydrofuran and added dropwise to a boiling suspension of 2.4 g of lithium aluminum hydride in 100 ml of tetrahydrofuran. After 3 hours, water is carefully added, the mixture is filtered, and the organic phase evaporated to dryness. The residue is taken up in 200 ml of diethyl ether and hydrogen chloride is introduced. The precipitate is filtered off and dried. 6.7 g (83%) of 1-(p-fluorophenyl-phenylmethyl)-3-methyl-3-(3,4-dimethoxybenzyl)-4-methylpiperazine-dihydrochloride (2b) are obtained. m.p. = 195° – 197° C. (ethanol)

In an analogous fashion, the compounds mentioned in Examples 2, 4 and 5 are obtained.

EXAMPLE 7

17 g of (D)-1-diphenylmethyl-3-methyl-3-(3,4-diacetoxybenzyl)-4-methylpiperazinone-(2) (cf. F) are dissolved in 100 ml of tetrahydrofuran and introduced dropwise with stirring during the course of an hour into a boiling suspension of 7.5 g of lithium aluminum hydride in 400 ml of tetrahydrofuran. After 3 hours, a solution of 80 g of tartaric acid in 125 ml of water is slowly added. After filtration, the tetrahydrofuran is distilled off in vacuum, the residue is combined with 350 ml of toluene, made alkaline with 20% ammonium hydroxide solution, and the organic phase is separated. The toluene solution is washed several times with water, dried over sodium sulfate, filtered, and evaporated in vacuum to dryness. The residue is taken up in isopropanol and combined with isopropanol/HCl and with diethyl ether. The precipitate is filtered off and dried in vacuum. 12.5 g (66.7%) of (D)-1-diphenylmethyl-3-methyl-3-(3,4-dihydroxybenzyl)-4-methylpiperazine-dihydrochloride (7aD) are obtained.
   m.p. = 176° – 178° C. (ethanol)
   $[\alpha]_D^{20} = + 11.2°$ (c = 10, methanol)

In the same fashion are obtained:
7aL)
   (L)-1-diphenylmethyl-3-methyl-3-(3,4-dihydroxybenzyl)-4-methylpiperazine-dihydrochloride
   m.p. = 178° C. (ethanol)
   $[\alpha]_D^{20} = - 11.3°$ (c = 10, methanol)
7bD)
   (D)-1-diphenylmethyl-3-methyl-3-(3,4-dihydroxybenzyl)-piperazine
   m.p. = 210° C. (isopropanol)

$[\alpha]_D^{20} = +19.5°$ (c = 10, methanol)

7bL)
(L)-1-diphenylmethyl-3-methyl-3-(3,4-dihydroxyben-zyl)-piperazine
m.p. = 211° C. (isopropanol)
$[\alpha]_D^{20} = -19.5°$ (c = 10, methanol)

EXAMPLE 8

7 g of 1-(p-fluorophenyl-phenylmethyl)-3-methyl-3-(3,4-dimethoxybenzyl)-piperazinone-(2) (Eb) are reacted with 1.8 g of lithium aluminum hydride according to Example 1. The crude product so obtained is dissolved in diethyl ether. Hydrogen chloride is introduced into the solution and the precipitate is filtered off and dried. 6.8 g (86%) of 1-(p-fluorophenyl-phenylmethyl)-3-methyl-3-(3,4-dimethoxybenzyl)-piperazine-dihydrochloride (1a) are obtained. m.p. = 188° - 190° C. (acetone)

In an analogous fashion, the remaining compounds mentioned in Example 1 are obtained.

EXAMPLE 9

Using a tablet press, tablets of the following composition were formed in the usual manner:

| | |
|---|---|
| 200 mg | (L)-1-(p-fluorophenyl-phenylmethyl)-3-methyl-3-(3,4-dimethoxybenzyl)-piperazine |
| 150 mg | corn starch |
| 13.50 mg | gelatin |
| 45 mg | milk sugar |
| 22.5 mg | talc |
| 2.25 mg | "Aerosil" (chemically pure silic acid in a sub-microscopically-fine subdivision) |
| 6.75 mg | potato starch (as a 6% paste) |

EXAMPLE 10

In the usual fashion dragées of the following composition were prepared:

| | |
|---|---|
| 100 mg | (L)-1-(p-fluorophenyl-phenylmethyl)-3-methyl-3-(3,4-dimethoxybenzyl)-4-methylpiperazine |
| 170 mg | core mass |
| 160 mg | sugaring mass |

The core mass comprises 9 parts of corn starch, 3 parts of milk sugar, and 1 part of "Luviskol VA 64" (vinylpyrrolidone-vinylacetate copolymer 60:40, cf. Pharm. Ind. 1962, 586). The sugaring mass comprises 5 parts of cane sugar, 2 parts of corn starch, 2 parts of calcium carbonate and 1 part of talc. The dragées so prepared are subsequently provided with a coating which is resistant to stomach juice.

EXAMPLE 11

50 g of (D)-1-diphenylmethyl-3-methyl-3-(3-hydroxy-4-methoxy-benzyl)-4-methylpiperazine-diamidosulfonate are dissolved in 5 liters of water. The solution is adjusted to a pH of 4.0 with 0.1 N sodium acetate and then made isotonic with sodium chloride. Thereafter it is filled into sterile ampules of 2 ml volume.

What is claimed is:

1. A piperazine compound of the formula

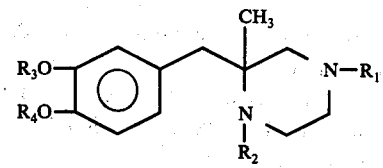

or a salt thereof with a physiologically tolerable acid, wherein $R_1$ is diphenylmethyl or diphenylmethyl wherein a hydrogen atom in the phenyl groups thereof may be replaced by fluorine; $R_2$ is hydrogen or methyl; and $R_3$ and $R_4$ are hydrogen or alkyl having 1-4 carbon atoms, but wherein at least one of $R_3$ and $R_4$ is hydrogen when $R_1$ is diphenylmethyl.

2. A compound as in claim 1 which is (D)-1-diphenylmethyl-3-methyl-3-(3-methoxy-4-hydroxybenzyl)-piperazine.

3. A compound as in claim 1 which is (L)-1-diphenylmethyl-3-methyl-3-(3-methoxy-4-hydroxybenzyl)-piperazine.

4. A compound as in claim 1 which is (D)-1-diphenylmethyl-3-methyl-3-(3-hydroxy-4-methoxybenzyl)-piperazine.

5. A compound as in claim 1 which is (L)-1-diphenylmethyl-3-methyl-3-(3-hydroxy-4-methoxybenzyl)-piperazine.

6. A compound as in claim 1 which is 1-(p-fluorophenyl-phenylmethyl)-3-methyl-3-(3,4-dimethoxybenzyl)-piperazine.

7. A compound as in claim 1 which is (D)-1-(p-fluorophenyl-phenylmethyl)-3-methyl-3-(3,4-dimethoxybenzyl)-piperazine.

8. A compound as in claim 1 which is (L)-1-(p-fluorophenyl-phenylmethyl)-3-methyl-3-(3,4-dimethoxybenzyl)-piperazine.

9. A compound as in claim 1 which is 1-(p,p'-difluorodiphenylmethyl)-3-methyl-3-(3,4-dimethoxyphenyl)-piperazine.

10. A compound as in claim 1 which is (D)-1-(p,p'-difluorodiphenylmethyl)-3-methyl-3-(3,4-dimethoxybenzyl)-piperazine.

11. A compound as in claim 1 which is (L)-1-(p,p'-difluorodiphenylmethyl)-3-methyl-3-(3,4-dimethoxybenzyl)-piperazine.

12. A compound as in claim 1 which is (D)-1-(p-fluorophenyl-phenylmethyl)-3-methyl-3-(3,4-diethoxybenzyl)-piperazine.

13. A compound as in claim 1 which is (L)-1-(p-fluorophenyl-phenylmethyl)-3-methyl-3-(3,4-diethoxybenzyl)-piperazine.

14. A compound as in claim 1 which is 1-(p,p'-difluorodiphenylmethyl)-3-methyl-3-(3,4-diethoxybenzyl)-piperazine.

15. A compound as in claim 1 which is (D)-1-(p,p'-difluorodiphenylmethyl)-3-methyl-3-(3,4-diethoxybenzyl)-piperazine.

16. A compound as in claim 1 which is (L)-1-(p,p'-difluorodiphenylmethyl)-3-methyl-3-(3,4-diethoxybenzyl)-piperazine.

17. A compound as in claim 1 which is 1-(p,p'-difluorodiphenylmethyl)-3-methyl-3-(3,4-dimethoxybenzyl)-4-methylpiperazine.

18. A compound as in claim 1 which is (D)-1-(p,p'-difluorodiphenylmethyl)-3-methyl-3-(3,4-dimethoxybenzyl)-4-methylpiperazine.

19. A compound as in claim 1 which is (L)-1-(p,p'-difluorodiphenylmethyl)-3-methyl-3-(3,4-dimethoxybenzyl)-4-methylpiperazine.

20. A compound as in claim 1 which is 1-(p-fluorophenylphenylmethyl)-3-methyl-3-(3,4-dimethoxybenzyl)-4-methylpiperazine.

21. A compound as in claim 1 which is (D)-1-(p-fluorophenyl-phenylmethyl)-3-methyl-3-(3,4-dimethoxybenzyl)-4-methylpiperazine.

22. A compound as in claim 1 which is (L)-1-(p-fluorophenyl-phenylmethyl)-3-methyl-3-(3,4-dimethoxybenzyl)-4-methylpiperazine.

23. A compound as in claim 1 which is (D)-1-(p-fluorophenyl-phenylmethyl)-3-methyl-3-(3,4-diethoxybenzyl)-4-methylpiperazine.

24. A compound as in claim 1 which is (L)-1-(p-fluorophenyl-phenylmethyl)-3-methyl-3-(3,4-diethoxybenzyl)-4-methylpiperazine.

25. A compound as in claim 1 which is 1-(p,p'-difluorodiphenylmethyl)-3-methyl-3-(3,4-diethoxybenzyl)-4-methylpiperazine.

26. A compound as in claim 1 which is (D)-1-(p,p'-difluorodiphenylmethyl)-3-methyl-3-(3,4-diethoxybenzyl)-4-methylpiperazine.

27. A compound as in claim 1 which is (L)-1-(p,p'-difluorodiphenylmethyl)-3-methyl-3-(3,4-diethoxybenzyl)-4-methylpiperazine.

28. A compound as in claim 1 which is (D)-1-diphenylmethyl-3-methyl-3-(3-methoxy-4-hydroxybenzyl)-4-methylpiperazine.

29. A compound as in claim 1 which is (L)-1-diphenylmethyl-3-methyl-3-(3-methoxy-4-hydroxybenzyl)-4-methylpiperazine.

30. A compound as in claim 1 which is (D)-1-diphenylmethyl-3-methyl-3-(3-hydroxy-4-methoxybenzyl)-4-methylpiperazine.

31. A compound as in claim 1 which is (L)-1-diphenylmethyl-3-methyl-3-(3-hydroxy-4-methoxybenzyl)-4-methylpiperazine.

32. A compound as in claim 1 which is 1-(p-fluorophenylphenylmethyl)-3-methyl-3-(3,4-dimethoxybenzyl)-4-methylpiperazine.

33. A compound as in claim 1 which is (D)-1-diphenylmethyl-3-methyl-3-(3,4-dihydroxybenzyl)-4-methylpiperazine.

34. A compound as in claim 1 which is (L)-1-diphenylmethyl-3-methyl-3-(3,4-dihydroxybenzyl)-4-methylpiperazine.

35. A compound as in claim 1 which is (D)-1-diphenylmethyl)-3-methyl-3-(3,4-dihydroxybenzyl)-piperazine.

36. A compound as in claim 1 which is (L)-1-diphenylmethyl-3-methyl-3-(3,4-dihydroxybenzyl)-piperazine.

37. A pharmaceutical composition comprising a compound or salt as in claim 1 in combination with a pharmaceutical carrier.

* * * * *